United States Patent [19]

Schwartz et al.

[11] 4,011,342
[45] Mar. 8, 1977

[54] METHOD AND COMPOSITION FOR THE TREATMENT OF HYPERTENSION WITH ORTHO-DISUBSTITUTED ARYLGUANIDINES

[75] Inventors: Jean Schwartz; Camille Georges Wermuth, both of Strasbourg, France

[73] Assignee: Seperic, Morat, Switzerland

[22] Filed: Feb. 26, 1975

[21] Appl. No.: 553,155

Related U.S. Application Data

[60] Division of Ser. No. 461,128, April 15, 1974, abandoned, which is a continuation of Ser. No. 258,050, May 30, 1972, abandoned.

[30] Foreign Application Priority Data

June 2, 1971 United Kingdom ............ 18510/71

[52] U.S. Cl. .............................................. 424/326
[51] Int. Cl.² ........................................ A61K 31/155
[58] Field of Search ........... 424/326; 260/565, 461, 260/128

[56] References Cited

FOREIGN PATENTS OR APPLICATIONS 667,116  2/1952  United Kingdom ............... 260/565

OTHER PUBLICATIONS

Chem. Abstr., vol. 48, col. 2629(c), 1948.
Chem. Abstr., vol. 68, col. 86760(g), 1968.
Chem. Abstr., vol. 66, col. 75768(c), 1967.

*Primary Examiner*—Albert T. Meyers
*Assistant Examiner*—Daren M. Stephens
*Attorney, Agent, or Firm*—Young & Thompson

[57] ABSTRACT

The guanidines of formula

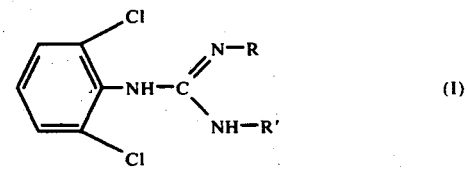

in which R and R' are each hydrogen or methyl and the pharmaceutically acceptable acid addition salts thereof exhibit hypotensive effects.

2 Claims, 1 Drawing Figure

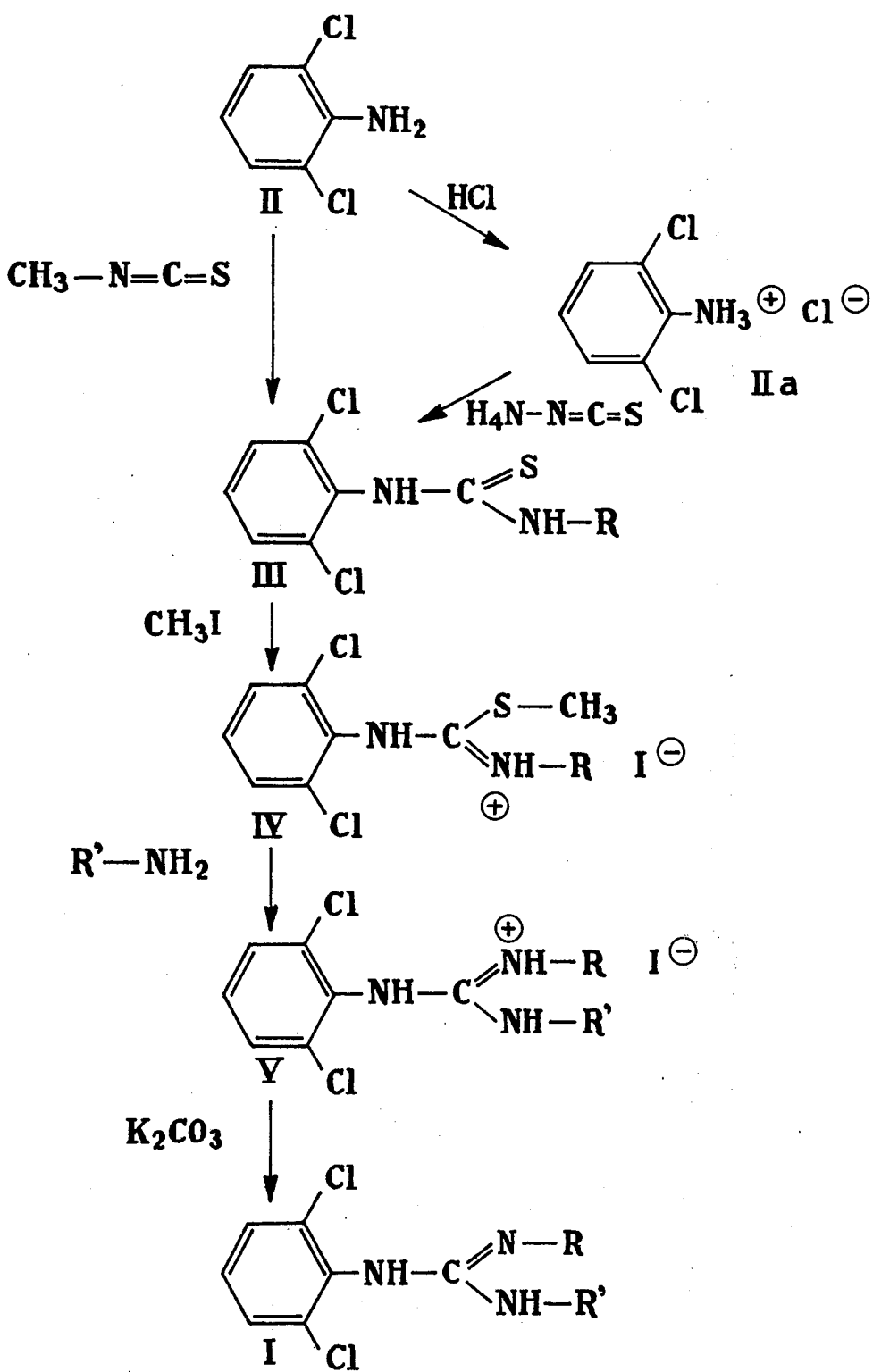

METHOD AND COMPOSITION FOR THE TREATMENT OF HYPERTENSION WITH ORTHO-DISUBSTITUTED ARYLGUANIDINES

This is a division, of application Ser. No. 461,128, filed Apr. 15, 1974, and now abandoned, which is a continuation of Ser. No. 258,050, May 30, 1972, abandoned.

This invention relates to new guanidines, having the general formula:

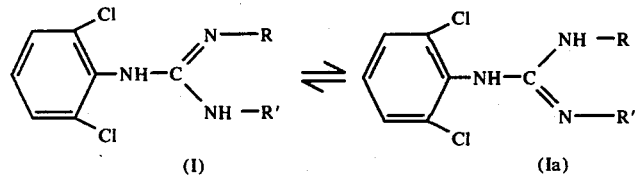

in which R and R', which are the same or different, are hydrogen or a methyl radical, together with their acid addition salts with pharmaceutically acceptable acids.

The formulae I and Ia correspond to the tautomeric forms of these guanidines. The following description will be made with reference only to the formula I.

Compounds (I) are thus (2,6-dichloro-phenyl)guanidine (R = R' = H), 3-(2',6'-l dichloro-phenyl)-1-methyl guanidine (R = H; R' = CH$_3$) and 3-(2',6'-dichloro-phenyl)-1,2-dimethyl guanidine (R = R' = CH$_3$).

These compounds may be prepared according to the process illustrated in the accompanying drawing.

According to this process, ammonia or methylamine, i.e., a compound of the formula R'-NH$_2$, is reacted with a N-(2,6-dichloro-phenyl)S-methyl isothiourea N'-substituted with the desired R group.

The S-methyl isothiourea is preferably used as the hydroiodide (compound IV) and the reaction with compound R'NH$_2$ is advantageously effected within a solent, such as an alkanol. This reaction is promoted by heating at a temperature of 80°–120° C, under the pressure generated by this temperature.

This reaction gives the hydroiodide of desired compound (V), which may be converted to the free base (I) by alkalinization, for example with potassium carbonate. This free base may in turn be converted to any desired salt by means of an acid.

The S-methyl-isothioureas (IV) are themselves obtained in known manner, from 2,6-dichloro-aniline (II), either by direct treatment with methyl isothiocyanate when it is desired to obtain the 2-methylated isothiourea (III, R = CH$_3$), or by treating 2,6-dichloro-aniline hydrochloride (IIa) with ammonium isothiocyanate when it is desired to obtain the isothiourea non-methylated at 2-position (III, R = H). The resulting intermediates III, on treatment with methyl iodide, give S-methylisothioureas (IV).

Guanidines I or the salts thereof exhibit hypotensive effects, derived from both direct and indirect α sympatholytic activity.

The following examples illustrate the invention:

EXAMPLE I

Synthesis of (2,6-dichloro-phenyl)guanidine and its hydrochloride (Formula I: R = R' = H)

In a pre-cooled bomb are introduced 13.4 g of N-(2,6-dichloro-phenyl)-S-methyl-isothiouronium hydroiodide (IV : R = H), prepared in known manner, followed by a solution of 300 ml of anhydrous ethanol saturated in the cold with ammonia. The bomb is heated at 110° C during 3 hours, with mechanical stirring. The solution is collected and is then evaporated to dryness. The resulting off-white crystals are taken up into water and ether; the aqueous phase which contains the (2,6-dichloro-phenyl)-guanidine hydroiodide (V : R = R' = H) is separated and is then made alkaline with potassium carbonate. The resulting material is extracted with ether, dried and evaporated, to give 1.5 g of (2,6-dichloro-phenyl) guanidine (I : R = R' = H), M.P. = 213° C.

| Analysis | | calculated | found |
|---|---|---|---|
| C | = | 41.18% | 41.14% |
| H | = | 3.45% | 3.51% |
| N | = | 20.58% | 20.41% |

To prepare the hydrochloride, 5.2 g of the above base are dissolved in isopropanol and 2.15 ml hydrochloric acid are added thereto. The solution is allowed to crystallize in a freezer, the resulting white crystals are filtered off and are then recrystallized from isopropanol. After evaporating in vacuo at 130° C during 25 minutes, there are obtained 4.4 g of (2,6-dichloro-phenyl)-guanidine hydrochloride, m.p. = 250° C.

| Analysis | | calculated | found |
|---|---|---|---|
| C | = | 34.95% | 35.25% |
| H | = | 3.35% | 3.51% |
| N | = | 17.47% | 17.62% |

EXAMPLE II

Synthesis of 1-methyl-3-(2',6'-dichloro-phenyl)-guanidine and its hydrochloride (Formula I : R = H; R' = CH$_3$)

20 g of N-(2,6-dichloro-phenyl)-S-methyl-isothiouronium hydroiodide (IV : R = H), prepared in known manner, followed by 250 ml ethanol and 20 ml of a 33% methylamine solution are introduced in a bomb. The reaction mixture is heated at 100° C during 60 hours, and is then evaporated to dryness. The residue is taken up into water and ether. The aqueous phase, which contains the 1-methyl-3-(2',6'-dichloro-phenyl)-guanidine hydroiodide (V : R'= CH$_3$), is cooled and potassium carbonate is then added to highly alkaline pH. The resulting material is extracted with ether, dried and filtered, and the ether phase is then evaporated to dryness. The product collected is recrystallized from isopropanol, to give 7.5 g of 1-methyl-3-(2',6'-dichloro-phenyl)guanidine (I : R = H; R' = CH$_3$), m.p. 140° C.

| Analysis | | calculated | found |
|---|---|---|---|
| C | = | 44.04% | 44.13% |
| H | = | 4.03% | 4.16% |
| N | = | 19.26% | 19.21% |

To prepare the hydrochloride, 8.4 g of the above base are dissolved in isopropanol. 3.6 ml of concentrated hydrochloric acid are added thereto, and the reaction mixture is left several hours in the refrigerator. The resulting crystals are filtered, recrystallized from isopropanol, filtered and dried under high vacuum, to give 7 g of 1-methyl-3-(2',6'-dichloro-phenyl)-guanidine, m.p. = 225° C.

| Analysis | | calculated | found |
|---|---|---|---|
| C | = | 37.74% | 37.94% |
| H | = | 3.96% | 4.13% |
| N | = | 16.50% | 16.50% |

EXAMPLE III

Synthesis of 1,2-dimethyl-3-(2',6'-dichloro-phenyl)-guanidine (Formula I : R = R' = $CH_3$) and its hydrochloride a. Synthesis of N-methyl-N'-(2,6-dichloro-phenyl)-thiourea (III : R = $CH_3$)

130 g of 2,6-dichloro-aniline, 100 g of methyl isothiocyanate and 300 ml of 95% ethanol are refluxed during 14 hours, with stirring. The resulting solution is cooled in the freezer: the white solid formed is filtered and washed with isopropyl oxide. After recrystallization from isopropanol, 65 g of product (III : R = $CH_3$), m.p. = 184° C, are collected.

| Analysis | | calculated | found |
|---|---|---|---|
| C | = | 40.86% | 40.72% |
| H | = | 3.44% | 3.48% |
| N | = | 11.96% | 11.89% | b. Synthesis of S,N-dimethyl-N'-(2,6-dichloro-phenyl)-isothiouronium hydroiodide (IV : R = $CH_3$)

65 g of the above product (III), 500 ml of methanol and 25 ml of methyl iodide are refluxed during 3 hours, with stirring. After evaporation of the methanol, the resulting yellowish material is recrystallized from isopropanol. It is then filtered and washed with isopropyl oxide. There are collected 82 g of product (IV : R = $CH_3$), m.p. = 96° C.

| Analysis | | calculated | found |
|---|---|---|---|
| C | · = | 28.64% | 28.50% |
| H | = | 2.91% | 2.97% |
| N | = | 7.42% | 7.41% | c. Synthesis of 1,2-dimethyl-3-(2',6'-dichloro-phenyl)-guanidine (I : R = R' = $CH_3$)

20 g of the above product IV, 250 ml of absolute ethanol and 20 ml of aqueous 33% methylamine solution are introduced in a bomb. This is then left during 60 hours at 90° C. After cooling, the solution is collected and evaporated to dryness in vacuo. The resulting greyish solid is stirred with distilled water and ether. The aqueous phase is collected and treated with a saturated potassium carbonate solution. It is then extracted with ether, dried over magnesium sulfate, and the ether is evaporated off in vacuo. The resulting material is recrystallized from the minimum amount is isopropanol. After drying, there are collected 5.4 g of product I (R = R' = $CH_3$), m.p. 115° C.

| Analysis | | calculated | found |
|---|---|---|---|
| C | = | 46.56% | 46.51% |
| H | = | 4.77% | 4.91% |
| N | = | 18.10% | 17.96% |

To prepare the hydrochloride, 11 g of the above base are dissolved in the minimum amount of isopropanol and 4.25 ml of concentrated hydrochloric acid are added thereto with warming. After cooling, crystallization is initiated by scratching. After one hour, the white material formed is collected, filtered and dried, to give 1,2-dimethyl-3-(2',6'-dichloro-phenyl)guanidine hydrochloride (10.5 g), m.p. = 257° C.

| Analysis | | calculated | found |
|---|---|---|---|
| C | = | 40.24% | 40.04% |
| H | = | 4.50% | 4.50% |
| N | = | 15.65% | 15.56% |

The pharmacological effects of compounds I will be described below, taking unsubstituted guanidine (R = R' = H) as example thereof.

These effects were compared with those of clonidine, of the formula:

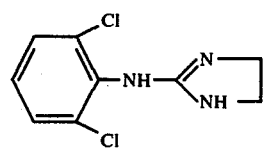

a substance of comparable structure used in human clinics for the treatment of hypertension.

A - Effects on the arterial pressure and on the nictitating membrane of anesthetized cat On traveneous injection at a dosage of 5 mg/kg, the product has a substantial hypotensive effect (drop of the arterial pressure of about 40 mm of Hg), and marked and durable α-adrenolytic (inhibition of the effects of adrenalin and noradrenalin on the arterial pressure and on the nictitating membrane) and α-sympatholytic (inhibition of the contraction of the nictitating membrane by pre- or post-ganglionic sympathetic stimulation) effects. Similar, although lesser, effects are noted after injection of 1 mg/kg.

Clonidine, injected at dosages of from 0.1 to 1 mg/kg produces essentially α-sympathomimetic effects on arterial pressure and on the nictitating membrane. It is only after a long hypertension phase that a slight tendency to hypotension is recorded. There is no adrenolytic or sympatholytic effect.

B - Effects on the preparation of isolated aorta of rabbit according to Furchgott At a concentration of 50 μg/ml, the product inhibits completely the noradrenalin-induced contraction of the aorta.

Clonidine has only α-sympathomimetic effects on this preparation, i.e., a strong contraction from a dosage of 5μg/ml.

C - Effects on two conventional tests adapted to evidence the depressant type action on the central nervous system in mice:

The rotarod test and extension of sleeping time test using chloral hydrate.

In both tests, the depressant action of clonidine is manifest at dosages of the order of 1 mg/kg while no action of this type is detected with the product up to a dosage of 50 mg/kg.

The other two guanidines I described above produce pharmacological effects of same type as those of guanidine taken as example. The acute toxicities of all three guanidines are equal to or lower than that of clonidine.

The results of such tests show that the pharmocoligical effects of the compounds according to the invention are distinguished from those of clonidine, particularly by the presence of a highly marked α-sympatholytic action and by the absence of effect on the central nervous system. Both these characters represent interesting advantages from the standpoint of the application in the treatment of hypertension.

In such a treatment, the compounds may be administered orally or parenterally.

For the oral route, a suitable pharmaceutical form is that of tablets containing each from 5 to 20 mg of active ingredient.

For the parenteral route, injectable ampoules containing from 0.5 to 2 mg of active ingredient in aqueous solution may be used.

Having now described our invention what We claim as new and desire to secure by Letters Patent is:

1. An orally administrable therapeutical composition having a hypotensive activity containing from 5 to 20 mg of a compound selected from the group consisting of a guanidine of the formula:

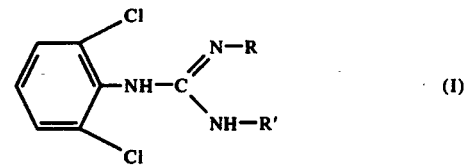

in which R and R' are each selected from the group consisting of hydrogen and methyl, and a pharmaceutically acceptable acid addition salt thereof, in a pharmaceutically acceptable carrier.

2. A parenterally administrable therapeutical composition having a hypotensive activity containing from 0.5 to 2 mg of a compound selected from the group consisting of a guanidine of the formula:

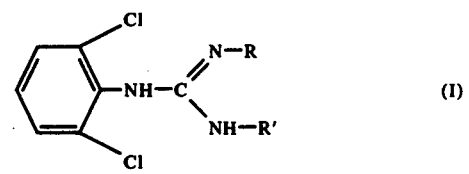

in which R and R' are each selected from the group consisting of hydrogen and methyl, and a pharmaceutically acceptable acid addition salt thereof, in a pharmaceutically acceptable carrier.

* * * * *